United States Patent [19]

Jannard

[11] Patent Number: 5,208,614
[45] Date of Patent: May 4, 1993

[54] CONCAVELY INDENTED LENSES FOR EYEWARE

[75] Inventor: James H. Jannard, San Juan Capistrano, Calif.

[73] Assignee: Oakley, Inc., Irvine, Calif.

[21] Appl. No.: 620,648

[22] Filed: Nov. 30, 1990

[51] Int. Cl.$^5$ ............................................. G02C 7/02
[52] U.S. Cl. .................................. 351/41; 351/158; 351/159
[58] Field of Search ............... 351/158, 159, 41, 43, 351/44

[56] References Cited

U.S. PATENT DOCUMENTS

| | | | |
|---|---|---|---|
| 289,301 | 4/1987 | Jannard | D16/112 |
| 293,450 | 12/1987 | Jannard | D16/112 |
| 322,975 | 1/1992 | Bolle | D16/102 |
| 4,515,448 | 5/1985 | Tackles | 351/41 |
| 4,674,851 | 6/1987 | Jannard | 351/41 |
| 4,779,291 | 10/1988 | Russell | 351/41 |
| 4,843,655 | 7/1989 | Hegendorfer | 2/449 |

FOREIGN PATENT DOCUMENTS 1249275 11/1959 France.

OTHER PUBLICATIONS

P. 46 of Runner's World, Jul., 1990.

Primary Examiner—Scott J. Sugarman

[57] ABSTRACT

Disclosed is an arcuately molded lens for use in active eyewear, having along the bottom edge of each right and left lens regions at least one downwardly concave indented area. The indented area may extend across the entire bottom edge of each lens region or it may only extend along a portion of the lens region. Where there is only one concavity per lens region, it may be placed anywhere along the bottom edge of the lens, near the midpoint, center or periphery. The lens may also have multiple concave indentations along its bottom edge.

25 Claims, 4 Drawing Sheets

CONCAVELY INDENTED LENSES FOR EYEWARE

BACKGROUND OF THE INVENTION

This invention relates generally to lenses used in eyewear suitable for active sports, and more particularly, to functional improvements attributable to the shape of the bottom edge of such lenses.

Eyewear typically worn during active sports such as hiking, skiing and bicycle racing is commonly designed to conform closely to the front and sides of the wearer's head. It is advantageous in such low profile eyewear to use arcuately molded lenses. Notwithstanding certain advantages attributable to the close fit, such as peripheral light interception and aerodynamic efficiency, sufficient ventilation may be impaired, resulting in the wearer being uncomfortable and possibly having impaired vision from fogging of the eyewear lenses. Prior efforts to alleviate this problem have been disclosed in U.S. Pat. Nos. 4,859,048 and 4,867,550, but they are by no means exclusive. The present invention offers an additional means to achieve the desired goals of providing comfort and optimum visibility without diminishing the advantages attendant in arcuately formed eyewear used for participation in active sports.

SUMMARY OF THE INVENTION

There has been provided, in accordance with one aspect of the present invention, an arcuately molded lens for use in eyewear suitable for participation in active sports. The lens has a top edge and a bottom edge having a nose opening for mounting the lens on the nose of a wearer and for defining a right and a left lens region. In one embodiment, there is a nose piece disposed in the nose opening. Over the nose opening in the lens there is a bridge portion. The distance separating the lower edge of the bridge portion and the top edge of the lens is defined as d1 and the distance separating the top edge of the lens and the lowest bottom edge of the lens is defined as d2. d1 is in the range of about $\frac{1}{4}$ inch to $1\frac{3}{4}$ inches, and d2 is in the range of about $1\frac{1}{4}$ inches to 3 inches. The lens also has an arcuate horizontal cross sectional configuration, wherein its arc length (L1) is in the range of from about 5 inches to about 7 inches. The bottom edge of each right and left lens region is concavely indented. There may be more than one concave indentation per each lens region. The concavely indented regions have a depth dimension within the range of about 1/32 inch to about $1\frac{1}{2}$ inches. The sum of the areas of the indentations in a given lens pane in this embodiment may be between approximately 1% and 50% of the remaining area of the surface of that lens pane.

The lens of the present invention has an inner concave surface and an outer convex surface and a thickness there between. The thickness of the lens may be substantially constant throughout or may in at least one portion of each distal region be less than the thickness of the lens in its central region. The thickness of the lens at the midpoint of the central region may taper gradually to a reduced thickness in the distal regions.

In one embodiment of the present invention, the arcuate cross sectional configuration of the lens in its molded condition substantially conforms to the surface of a cylinder. The radius from the axis of the cylinder to an arc defining the inner concave surface of the lens is a substantially constant radius in the range of from about $2\frac{1}{2}$ inches to about $4\frac{1}{2}$ inches. The radius of curvature of the lens along a horizontal plane may be defined by $R_2$, and the radius of curvature along a vertical plane through the lens may have a radius defined by $R_3$, and $R_2$ may be equal to or less than $R_3$. In another embodiment, $R_2$ is in the range of from about two inches to about four inches, and $R_3$ is greater than or equal to $1.10 R_2$.

The lenses of the present invention may be mounted in a pair of eyeglasses, by pivotably attaching a right and a left earstem to each lens region. Alternatively, the lenses of the present invention may be secured to an upper frame, and earstems are pivotably secured to that frame.

In a further embodiment of the present invention, the lenses described above may be adapted to be used in a dual lens eyewear system suitable for participation in active sports.

DETAILED DESCRIPTION OF THE PREFERRED EMBODIMENTS

Figure 1:
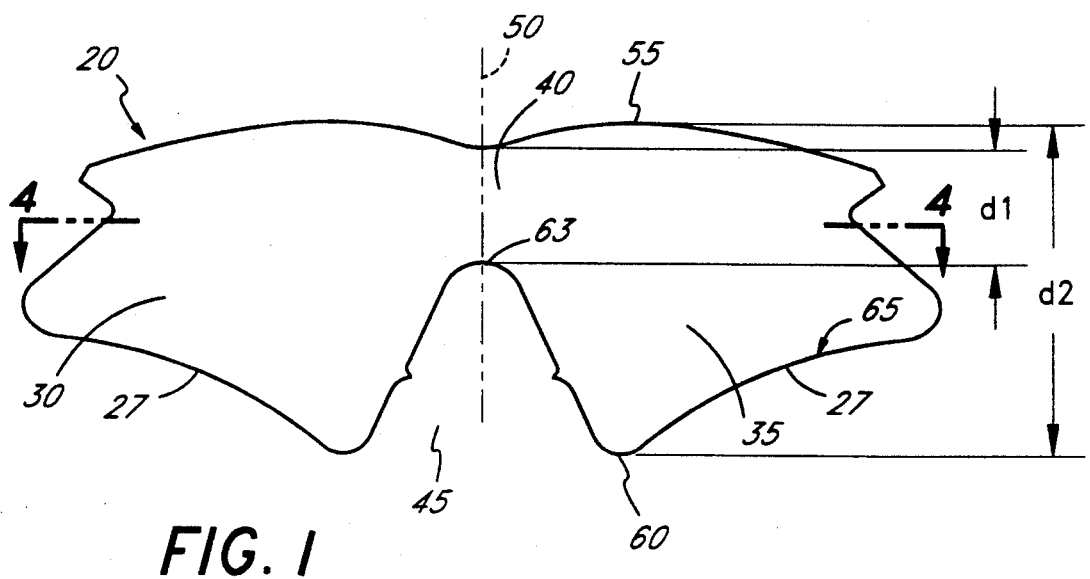
FIG. 1 is a front elevational view of a lens of the present invention in a flattened condition.
Figure 2:
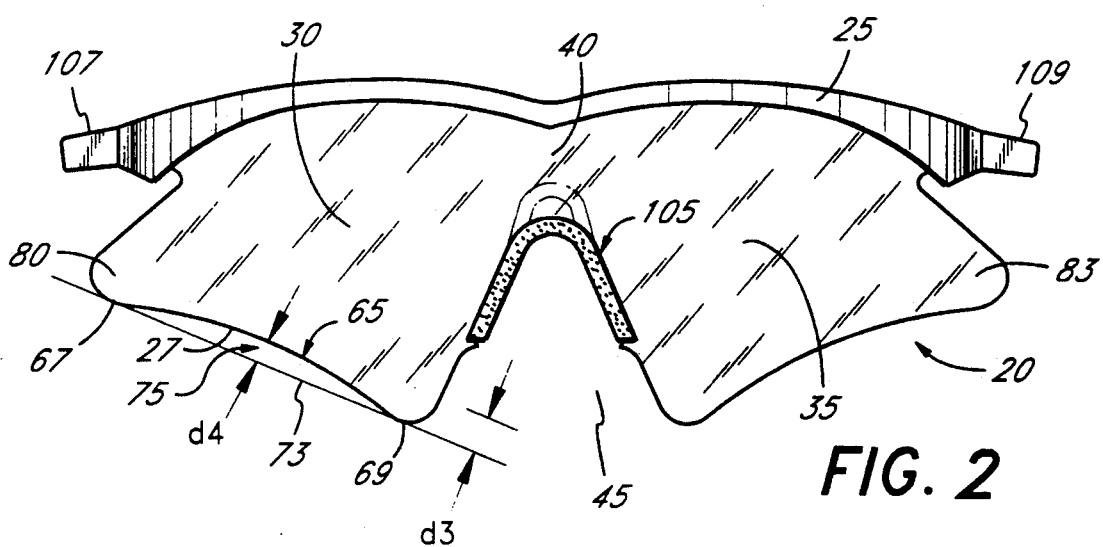
FIG. 2 is a front elevational view of a lens of the present invention, having a frame attached and showing a measurement of the extent of indentation.
Figure 3:
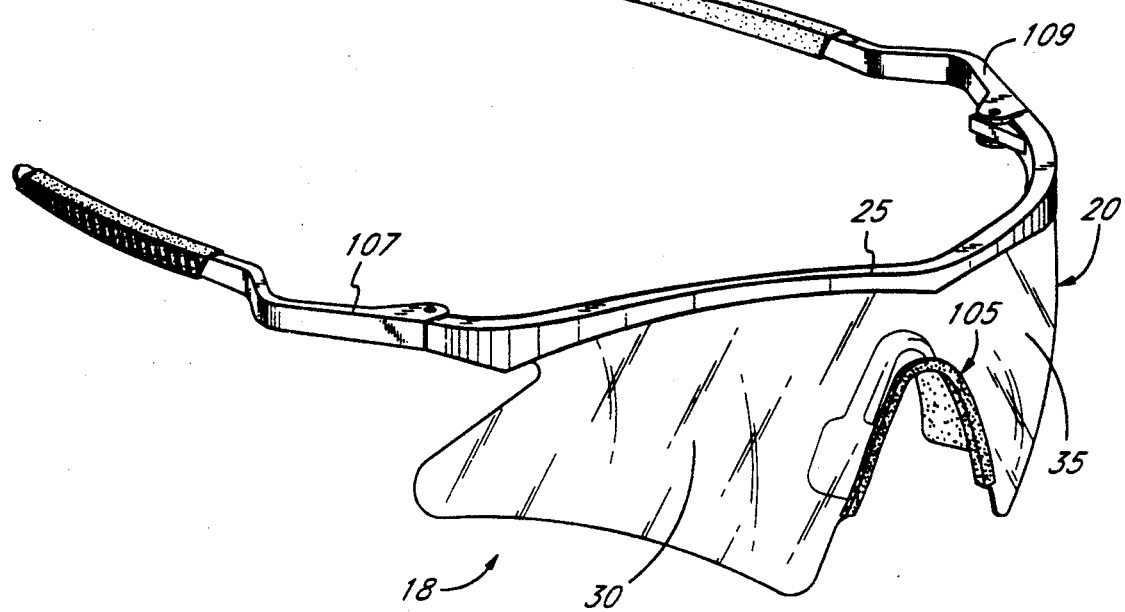
FIG. 3 is a front perspective view showing a lens of the present invention as part of an eyewear system.

Referring to FIGS. 1-3, there has been provided in accordance with one aspect of the present invention a lens 20 for mounting in a frame 25 to form eyewear 18 (FIG. 3), conformed to extend in the path of the wearer's left and right eye fields of vision. In particular, the invention relates to the indented or concave opening downward shape of the lower edge of the lens. The shape of one embodiment of the lens of the present invention is best understood by reference to FIG. 1, which illustrates a relatively smoothly curved, single, concave indentation 27 in each lens pane 30, 35. However, lenses of many other shapes may be envisioned having irregularly shaped indentations or multiple concave indentations for each eye pane (see FIG. 10), which will accrue the advantages of the present invention.

Lenses in accordance with the present invention can be manufactured by any of a variety of processes well known in the art. Preferably, the lens is injection molded and comprises a relatively rigid and optically acceptable material such as polycarbonate. The indentation 27 can be formed in the molding, cutting, or stamping process used to form the lens, or, preferably, is machined into a previously molded lens blank.

Alternatively, the lens can be stamped or cut from flat sheet stock and bent into a curved configuration. This curved configuration can then be maintained by the use of a relatively rigid, curved frame, or by heating the curved sheet to retain its curved configuration, as is well known in the thermoforming art.

A first eye pane 30 and a second eye pane 35 are located in front of the wearer's right and left eyes, respectively. A bridge portion 40 is provided to merge the first and second eye panes into a single lens. Beneath the bridge 40 there is provided a generally triangular nose opening 45. In another embodiment, the first and second panes are not merged into a single lens eyewear system, rather they consist of two separate lenses adapted for use in a dual lens system.

It is understood that the eye panes 30 and 35 will, in the preferred embodiment, be essentially mirror images of each other about a central vertical axis 50 (FIG. 1), and the discussion in connection with one is intended to apply to both. The maximum height $d_2$ of the lens 20 (see FIG. 1) of the present invention, measured from the top edge 55 of the lens 20 to the lowest point 60 along the bottom edge 65, may be varied to optimize aesthetic and functional considerations, but will typically fall within the range of from about 1 to 3 inches, preferably from about 1½ to about 2½ and most preferably between about 1½ to about 1¾ inches. The height $d_1$ of the lens 20, measured from the center of top edge 55 of the lens to the lower edge 63 of the bridge portion 40, may also vary, but preferably it is within the range of from about ¼ inch to ¾ inches and more preferably between about ½ and ¾ inch.

The bottom edge 65 of lens 20 is provided with at least one region 27 which is concave, opening in a downward direction. One embodiment of such a concave region is illustrated in FIG. 2 as extending between the lowest points of the concavity 67 and 69. As illustrated therein, the bottom edge 65 is concave in relation to an imaginary straight line 73 drawn between relative low points 67 and 69. Thus, the bottom edge 65 can be seen as diverging away from straight line 73 for a distance $d_3$ which is greater than zero at at least one point.

Thus, by "concave downward," "indented," "diverging away" and the like terms herein used, it is meant that an imaginary straight line 73 drawn between the two lowest points of a concave indentation 27, for example 67 and 69, defines a regular or irregular enclosure having an area 75 of greater than 0 square inches. A lens in which no straight line 73 can be positioned so as to define a closed area 75 thus does not have a "concavity" as intended herein. This is true of continuously convex prior art lenses, in which case the imaginary line 73 can only be drawn as a tangent to some point along the lower edge 65 of the lens. In a lens having a perfectly straight lower edge, line 73 can only be parallel or coextensive with the lower edge 65, thereby failing to produce a closed space having a positive area 75.

In a dual lens system, there are two distinct lenses, or lens panes, as is well understood. In connection with single lens systems, the singular terms "eye pane" or "lens pane" herein will refer to precisely half of the area of the overall single lens. Thus, a single lens system will be deemed for the present purpose to be comprised precisely of two equal eye panes.

The extent of the indentation 27 can be characterized in terms of the ratio of the area 75 to the remaining area of the associated eye pane. For example, the area 75 of the concavity preferably is within the range of from about 1% to about 100% of the remaining area of the eye pane. Thus, in the latter instance, the area 75 is precisely the same as the area of the associated eye pane. Preferably, the area of the concavity will be within the range of about 1% to about 30% of the remaining area of the associated eye pane, and more preferably within the range of from about 3% or 4% to about 10% of the area of the associated eye pane.

An alternative way to characterize the indentation 27 in the lens of the present invention is by the depth $d_3$ thereof along an axis perpendicular to the axis of the imaginary straight line 73. Since the indentation 27 by definition requires a distance between straight line 73 and the bottom edge 65 of the lens, the depth $d_3$ can be measured along a perpendicular line drawn between straight line 73 and at least some point along bottom edge 65. Since the depth $d_3$ will vary across the length of the concavity, it is convenient to measure the maximum depth $d_4$ for each concavity. The maximum depth $d_4$ is the deepest part of the concavity measured by a line drawn perpendicularly to straight line 73.

In a single concavity embodiment such as illustrated in FIG. 2, the depth $d_4$ is generally within the range of from about 1/64 of an inch to about one inch. Preferably, the depth will be in the range of from about 1/32 inch to about ½ inch, and most preferably between about ⅛ inch and about 3/16 inch, although in a design for applications where maximizing ventilation is deemed desirable, a minimum depth of at least about 3/16 inch will be used, and a minimum of at least about ¼ inch or even ⅜ inch may be desired.

The ventilation function will be maximized by a combination of factors, as will be understood by one of skill in the art in view of the teachings of this disclosure. For example, a lens with a relatively large vertical coverage of the face will tend to require a deeper $d_4$ dimension to achieve meaningful ventilation as compared to a relatively vertically narrow lens, the lower edge of which is already generally at or above the cheek bone. In a lens which has multiple concavities along the bottom edge of a single lens pane (FIG. 10), the depth $d_4$ of each individual concavity 110, 111, 112 will generally be less than the depth $d_4$ of the concavity in a single concavity lens pane.

Figure 10:
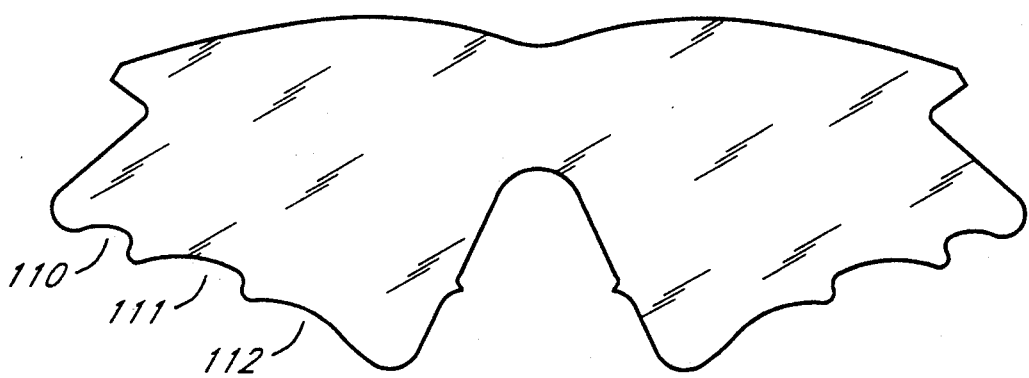
FIG. 10 is a front elevational view of a lens of the present invention having more than one concavity per lens pane.

The precise geometric profile of the indented regions may vary, and where there are more than one indented region per eye pane, they need not repeat the same shape (see FIG. 10).

Figure 4:
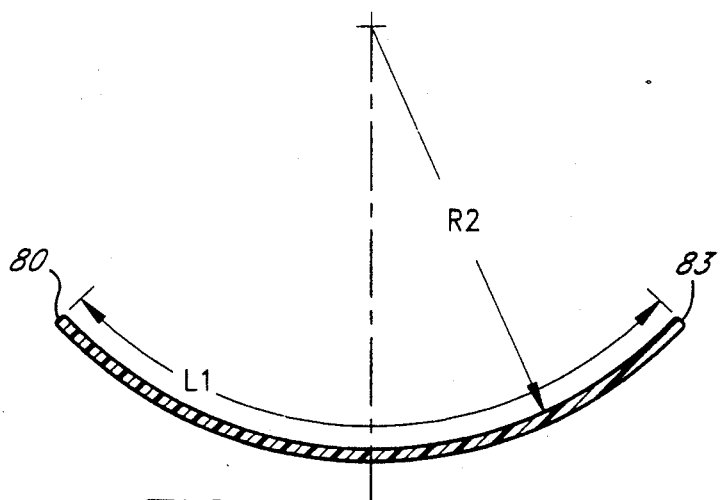
FIG. 4 is a section along lines 4—4 of FIG. 1 normal to the vertical axis of the lens, in its normal arcuate configuration.

In an embodiment where lower lens edge 65 defining the concave indentation 27 in the lens 20 has a curve of substantially constant radius throughout its arc length between low points 67 and 69, the radius of curvature is preferably within the range of from about 1 to about 12 inches, or more preferably from about 1½ to about 6 inches.

and contained by the axis 98 (FIG. 6) of the cylinder defined by the panes. The lens 20 has a horizontal length dimension $L_1$ (FIG. 4) between the generally rearwardly extending distal ends 80 and 83 which measures in the range of from about 5 inches to about 7 inches. The lens is further characterized by a radius $R_2$, detailed infra.

In the preferred embodiment of the present invention, the lens pane, be it single or adapted for use in a dual lens system, is arcuately formed. For example, the embodiments depicted in FIGS. 4, 5 and 6 exhibit cylindrical curvature along the horizontal plane, preferably imparted from the molding process. Note that panes 30 and 35 and distal ends 80 and 83 wrap backwardly or rearwardly to extend in the paths of the wearer's peripheral fields of vision, without such abruptly changing curvature as would distort the light passing through the side wrapping portions of the panes.

Figure 6:
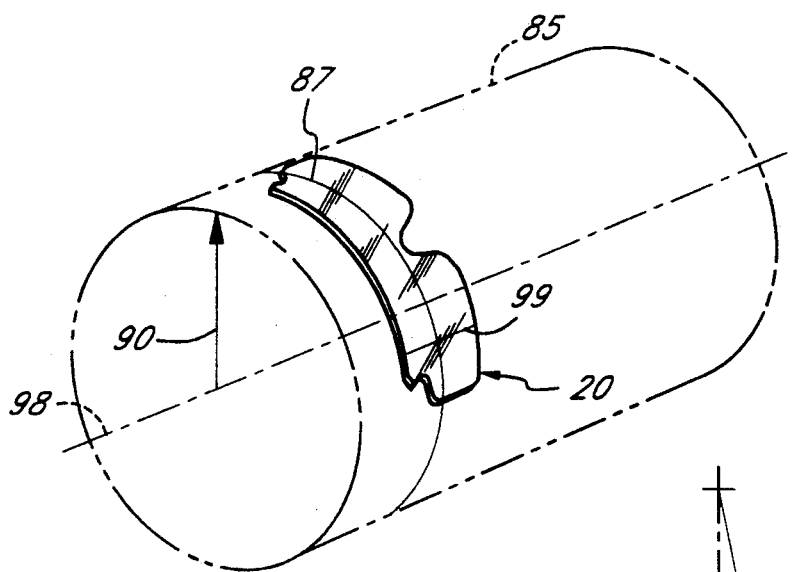
FIG. 6 is a perspective view of an arcuate lens of the present invention shown conforming to the surface of a cylinder.

FIG. 6 depicts a unitary lens of the present invention substantially conforming to the exterior surface of a cylinder 85. The benefits derived from a cylindrically shaped unitary lens are expounded in U.S. Pat. No. 4,859,048, which is incorporated herein by reference. Thus, one embodiment of the lens of the present invention is preferably provided with a substantially uniform curve, such that a line 87 (FIG. 6) drawn along the surface of the lens 20 in a circumferential direction defines an arc of substantially uniform radius 90. A line 99 drawn along the surface of the lens 20 in an axial direction is substantially parallel to the axis 98 of a cylinder 85.

Although a variety of radii might accrue the advantages of the present invention, the lens is preferably provided with a radius 90 within the range of from about 2½ to about 4½ inches, and preferably within the range of from about 3½ to 4 inches. The foregoing radius dimensions represent the distance from the axis 98 to the interior, concave surface of the lens.

Figure 7:
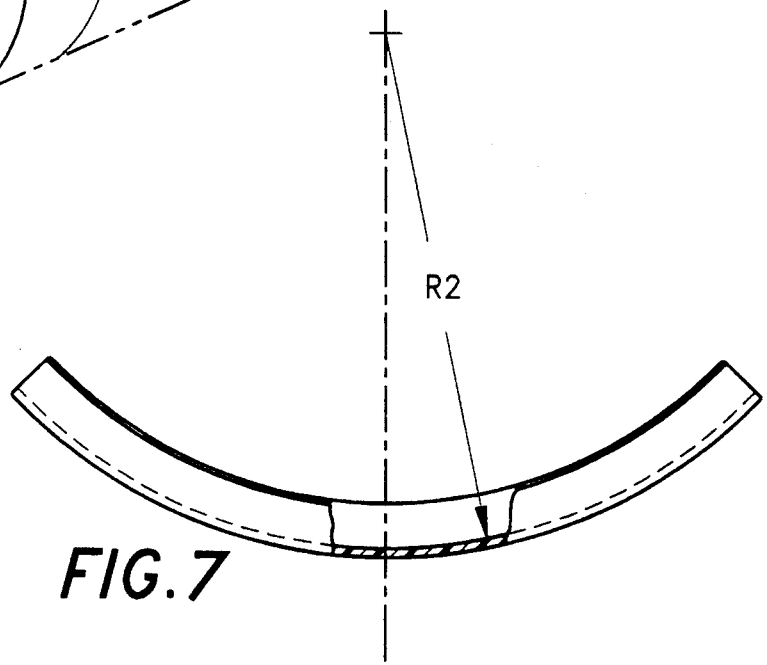
FIG. 7 is a top plan view of a lens of the present invention with the $R_2$ radius less than $R_3$.
Figure 8:
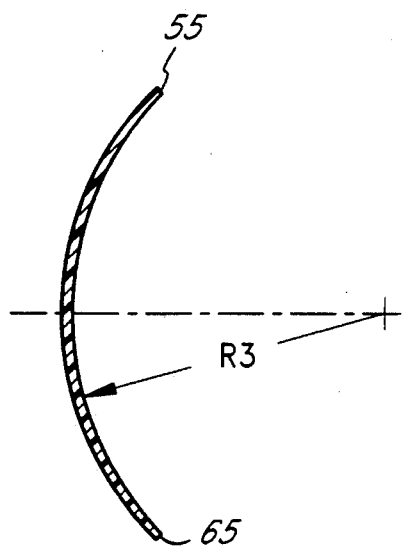
FIG. 8 is an elevational sectional view of the non-cylindrical embodiment of the lens illustrated in FIG. 7.

The lens of the present invention may alternatively be curved along each of two substantially perpendicular axes to produce a lens, for example, which conforms to the surface of generally toroidal configuration. Thus, a cross-section of the lens taken along a horizontal plane (not illustrated) midway from the bottom edge 65 of the lens to the top edge 55 will reveal an arcuate cross-sectional configuration, characterized by a first radius dimension $R_2$ as shown in FIG. 7. Unlike the cylindrical lens, however, a vertical cross-section through the lens reveals a curvature from top edge 55 to bottom edge 65 characterized by a second radius dimension $R_3$, as shown in FIG. 8. Where $R_2$ equals $R_3$, the lens will conform to the surface of a sphere. Where $R_2$ is less than $R_3$, the lens will conform to the surface of a toroid. Such toroidal lenses are the subject of U.S. Pat. No. 4,867,550 which is incorporated herein by reference.

The lens of the present invention has sufficient thickness that it is not accurately defined as having only a single radius. Instead, referring to FIG. 5, the lens 20 has a thickness or depth dimension 93 along its entire arc length which causes the arc defined by the outer, convex surface 95 to have an additional radius $R_1$ to the radius $R_2$ defined by the inner, concave surface 97 of lens 20. In an embodiment where the lens is of substantially uniform thickness throughout, and the axes are coincident, the radius $R_1$ of the convex surface 95 is essentially equal to the sum of the radius $R_2$ of the concave surface 97 and the depth 93 of the lens.

In accordance with another embodiment of the present invention, there has been provided a unitary lens substantially as any of those described above, with one following modification. Referring to the horizontal sectional view illustrated in FIG. 5, there is disclosed a lens 20 defined between an outer convex surface 95, having a radius $R_1$, and an inner concave surface 97, having a radius $R_2$. The principal difference from the previously detailed embodiment is that the thickness of the lens 20 at each of the distal ends 80 and 83 is less than the average thickness of the lens at every point intermediate the two distal ends 80 and 83. In addition, the thickness of lens 20 measured at at least one point intermediate the two ends 80 and 83 is greater than the thickness at each of those ends.

Figure 5:
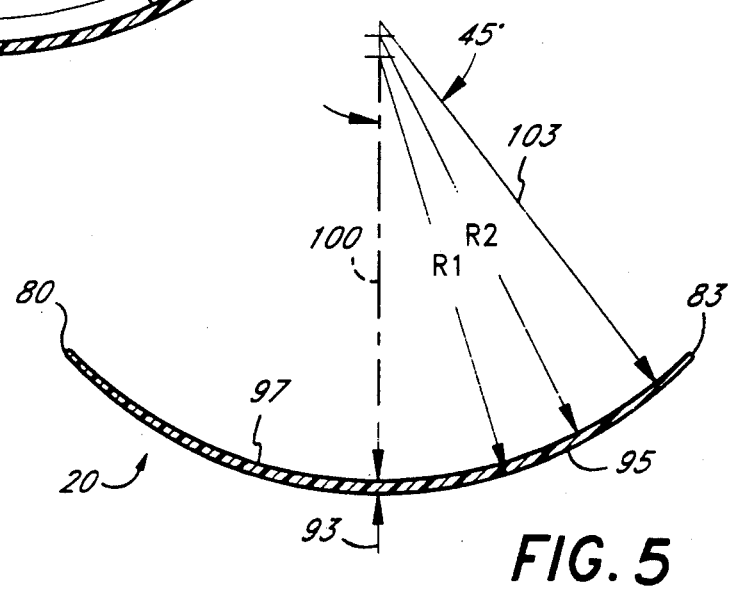
FIG. 5 is a sectional view like FIG. 4, of a tapered thickness embodiment of the lens of the present invention.

The invention can best be understood by reference to FIG. 5, which illustrates the relationship between the lens thickness and angular position along the arc length of a lens. Since the arc length of a lens can be varied considerably, although it is preferably within the range of from about 5½ to 7 inches, reference points will arbitrarily be selected at the centerline 100 and at the 45° line 103. Since the distance from centerline 100 to reference line 103 is ⅛ of 360°, the reference arc length for a radius of 3 inches is about 4.7 inches, which is below the preferred range, thus defining a reference point on the lens.

In accordance with the tapered lens embodiment of the present invention, the thickness of the lens at reference line 103 is preferably from about 40% to about 99% of the thickness at centerline 100. Thus, for example, a lens having a centerline thickness 100 of about 0.060 inches will preferably have a thickness of within the range of about 0.024 to about 0.059 inches at reference line 103, and a thickness near the distal end 83 of the lens within the range of about 0.020 to about 0.055 inch. The thickness of the lens at the midpoint is preferably within the range of from about 0.055 to about 0.070 inch.

Preferably, the thickness of the lens tapers at a substantially even rate from the widest region which is centered about the centerline 100, to narrower regions near each of the distal ends 80 and 83. In this manner, optical distortion is minimized. By even rate it is meant that the taper results from the convergence of an arc defining the outer convex surface 95 of lens 20, and an arc defining the inner concave surface 97 of lens 20, each arc characterized by constant radii $R_1$ and $R_2$, respectively. Although the surfaces need not be perfectly uniform arcs, as in the previously discussed embodiment, conformation of the lens surface to a substantially constant radius curve accrues optical advantages. The foregoing may be accomplished in a variety of ways, such as, for example, by making radius $R_1$ equal to radius $R_2$ and displacing the center points from each other. Alternatively, radius $R_1$ may be greater or lesser than radius $R_2$, so long as the converging geometry results.

In the production lens, of course, the distal ends 80 and 83 are formed well before the continuation of the arcs defining surfaces 95 and 97 converge. In a cylindrical lens produced in accordance with this embodiment, for example, and having a centerline thickness of approximately 0.060 inches, the thickness at a point proximate either distal end 80 or 83 will generally be within the range of from about 0.040 to about 0.055 inch.

Finally, since a portion of the lens 20 near the distal ends 80 and 83 serves primarily to block peripheral light and is likely outside of the wearer's direct line of vision, it is less important that the radius of curvature be constant in this area. Thus, the lens may be provided with a smooth taper only up to a certain transition point intermediate the reference line 103 in FIG. 5 and the distal end 83. From that transition point until the distal end 83, the lens 20 may be provided with a relatively constant thickness or a taper of a different rate.

Referring to FIG. 3, the lens of the present invention may be provided with a top frame 25 extending along and bounding the upper edge 55 of the lens, and secured by conventional means. Alternatively, the frame can bound the lower edge of the lens, the entire lens, or any other portion of the base as will be evident to those of skill in the art.

Preferably, the lens of the present invention is mounted in eyewear having no lower frame, thereby leaving the lower edge of the lens exposed. This reduces the weight and bulk of the eyewear, and allows maximization of ventilation through concavity 27. At the same time, the vertical height of the lens can be minimized while still optimizing the vertical field of view without obstruction from the lower frame. The frame advantageously consists of any of a variety of relatively rigid, molded thermoplastic materials which are well known in the art, and may be transparent or dyed any of a variety of colors.

A nosepiece 105 may be provided, as illustrated in FIGS. 2 and 3, which bounds the pane in the region of the nose opening 45. The nosepiece 105 preferably comprises a relatively soft elastomeric material having a coefficient of sliding friction that increases when the material is wetted. Such a material is preferably hydrophilic, and tends to retain the eyewear in position on the wearer's upper nose area as the wearer perspires or encounters moisture as during skiing. Also, the preferred material is soft, for comfort. One such material is KRATON G, a product of Shell Oil Company.

Figure 9:
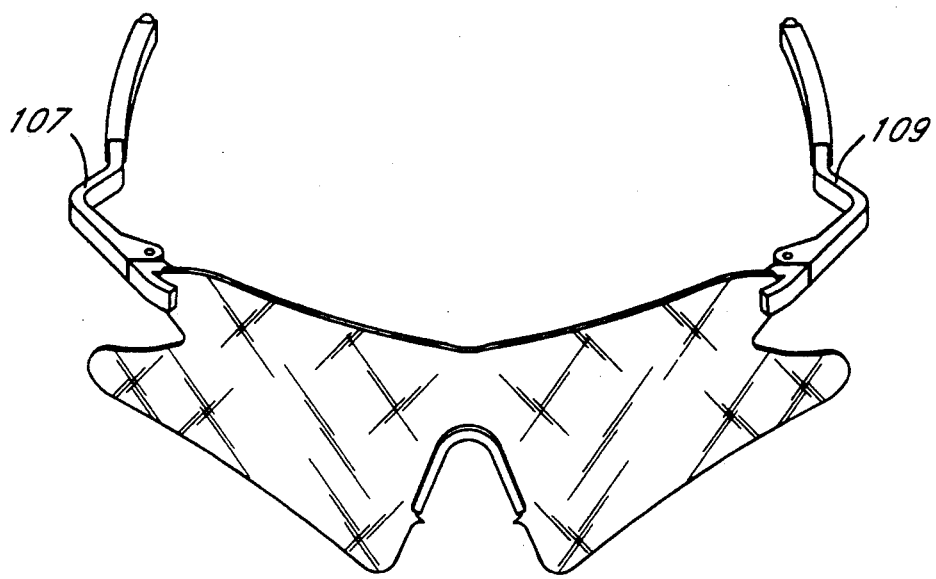
FIG. 9 is a front perspective view of assembled eyewear in accordance with one aspect of the present invention.

Finally, referring to FIGS. 2, 3 and 9, eyewear embodying the lens of the present invention are provided with a pair of earstems 107, 109. Earstems 107, 109 may be formed in the same manner as upper frame 25. Earstems 107, 109 may be pivotably secured to the lateral ends of an upper frame 25 (FIGS. 2 and 3) or to a frame which also or alternatively bounds the lower edge of the lens (not illustrated). Earstems 107, 109 may also be pivotably secured directly to the lens (FIG. 9) without the use of a conventional frame.

Although this invention has been described in terms of certain preferred embodiments, other embodiments that are apparent to those of ordinary skill in the art are also within the scope of this invention. Accordingly, the scope of this invention is intended to be limited only by the appended claims.

What is claimed is:

1. An arcuately molded lens for eyeglasses for participation in active sports, such as biking and skiing, said lens comprising:
   a top edge and a bottom edge, said bottom edge having a nose opening therein for mounting said lens on the nose of a wearer and for defining a right and a left lens region;
   said lens having a bridge portion over said nose opening, the distance separating the lower edge of said bridge portion and the top edge of the lens being defined as $d_1$ and the distance separating the top edge of the lens and the lowest bottom edge of the lens being defined as $d_2$, wherein d1 is in the range of about ¼ inch to about 1µ inches, and $d_2$ is in the range of about 1¼ inches to about 3 inches;
   said lens having an arcuate horizontal cross sectional configuration, wherein the arc length (L1) of said lens is in the range of from about five inches to about seven inches;
   wherein the bottom edge of each of said right and left lens regions is concavely indented, open in the downward direction, with a maximum indentation depth of no less than about 1/16 of an inch.

2. An arcuately molded lens for eyeglasses as in claim 1, wherein each of said concavely indented regions has a maximum depth within the range of from about 1/16 inch to about ½ inch.

3. An arcuately molded lens for eyeglasses as in claim 1, wherein at least two concavely indented regions are provided in each of said right and left lens regions.

4. The lens of claim 1, wherein the sum of the areas of the indentations in any one of said lens regions is between approximately 1% and 50% of the remaining area of said lens region.

5. An arcuately molded lens for eyeglasses as in claim 4, wherein each of said concavely indented regions has a depth within the range of about 1/32 inch to about 1¼ inches.

6. A pair of eyeglasses, comprising a right and left earstem pivotably attached to an arcuately molded lens, wherein said lens comprises a top edge and a bottom edge;
   said bottom edge having a nose opening therein for mounting said lens on the nose of a wearer and for defining a right and a left lens region;
   said lens having a bridge portion over said nose opening, the distance separating the lower edge of said bridge portion and the top edge of the lens being defined as $d_1$ and the distance separating te top edge of the lens and the lowermost bottom edge of the lens being defined as $d_2$, wherein $d_1$ is in the range of ¼ to about 1¾ inches, and $d_2$ is in the range of about 1¼ inches to about 3 inches,
   said lens having an arcuate horizontal cross sectional configuration, wherein the arc length (11) of said lens if in the range of from about five inches to about seven inches,
   wherein the bottom edge of each of said right and left lens regions is concavely indented, opnen in the downward direction, with a maximum indentation depth of no less than about 1/16 inch.

7. A pair of eyeglasses as in claim 6, further comprising an upper frame, wherein said earstems are pivotably secured to said upper frame and said upper frame is secured to said lens.

8. A pair of eyeglasses as in claim 6, further comprising an upper and a lower frame, wherein said earstems are pivotably secured to said upper frame and said upper frame is secured to said lens.

9. A pair of eyeglasses as in claim 6, further comprising a frame which surrounds said lens, wherein said earstems are pivotably secured to said frame and said frame is secured to said lens.

10. A lens for eyeglasses, said lens being suitable for participation in active sports, such as biking and skiing, comprising:
   an upper edge and a lower edge, said lower edge having a nose piece opening therein for mounting said lens on the nose of a wearer and for defining a right and a left lens region,
   said lens having an arcuate horizontal cross sectional configuration in its molded condition,
   said lens having an inner concave surface and an outer concave surface and a thickness there between,
   wherein the lower edge of each of said right and left lens regions is provided with at least one indentation having a depth no less than about 1/16 inch, thereby facilitating ventilation below and behind the lens.

11. The lens of claim 10, wherein said arcuate horizontal cross-sectional configuration of said lens is comprised of a central region and a first and second adjacent, distal regions, the thickness of said lens in at least one portion of each of said distal regions being less than the thickness of said lens in said central region.

12. The lens of claim 11, wherein the thickness of said lens at the midpoint of said central region tapers gradually to a reduced thickness in said distal regions.

13. The lens of claim 10, wherein the sum of the areas of said indentations in either of said left or right lens regions is between approximately 1% and 50% of the remaining area of said left of right lens region.

14. The lens of claim 13, wherein no more than one indentation is provided in each of said right and left lens regions.

15. The lens of claim 10, wherein said lens has an arcuate horizontal cross-sectional configuration in its molded condition which substantially conforms to the surface of a cylinder.

16. The lens of claim 15, wherein the radius from the axis of said cylinder to the inner concave surface of said lens is a substantially constant radius in the range of from about 2½ inches to about 4½ inches.

17. The lens of claim 10, wherein the radius of curvature of said lens along a horizontal plane is defined by $R_2$, the radius of curvature along a vertical plane through said lens has a radius defined by $R_3$, and wherein $R_2$ is equal to or less than $R_3$.

18. A lens as in claim 17, wherein $R_2$ is in the range of from about 2 inches to about 4 inches, and $R_3$ is greater than or equal to $1.10 R_2$.

19. A pair of eyeglasses, comprising:
a lens having an upper edge and a lower edge,
said lower edge having a nose piece opening therein for mounting said lens on the nose of the wearer and for defining a right and left lens region,
said lens having an arcuate horizontal cross sectional configuration in its molded condition,
said lens having an inner concave surface and an outer concave surface and a thickness therebetween,
wherein the lower edge of each of said right and left lens regions is provided with at least one indentation having a depth no less than about 1/16 inch, thereby facilitating ventilation below and behind the lens; and
a right and a left earstem pivotably attached to the lens.

20. A pair of eyeglasses as in claim 19, further comprising an upper frame, wherein said earstems are pivotably secured to said upper frame and said upper frame is secured to said lens.

21. A pair of eyeglasses as in claim 19, further comprising a nose piece disposed in the nose piece opening formed on the lower edge of said lens.

22. A pair of eyeglasses as in claim 19, further comprising a frame which surrounds said lens, wherein said earstems are pivotably secured to said frame and said frame is secured to said lens.

23. An eyeglass lens of the type adapted to be used in a dual lens eyewear system suitable for participation in active sports, such as biking and skiing, said lens comprising a top edge and bottom edge wherein the bottom edge of said lens is indented upwardly to form at least one downward facing concavity for facilitating ventilation between the bottom edge of the lens and the face of a wearer when said lens is mounted on a frame to form a pair of eyeglasses.

24. An arcuately molded lens for eyeglasses comprising a top edge and a bottom edge, said bottom edge having a nose piece opening formed therein for mounting said lens on the nose of a wearer and for defining a right and a left lens region, the improvement comprising at least one concave ventilation indentation in the bottom edge of each of said right and left lens regions.

25. An arcuately molded lens for eyeglasses comprising a lens having a top edge and a bottom edge, said bottom edge having a nose piece opening formed therein for mounting said lens on the nose of a wearer and for defining a right and a left lens region, and wherein said lens has a bridge portion over said nose piece opening, the distance separating the lower edge of said bridge portion and the top edge of the lens being defined as $d_1$ and the distance separating the top edge of the lens and the bottom edge of the lens being defined as $d_2$, wherein $D_1$ is in the range of about 178 inch to 1¾ inches, and $d_2$ is in the range of about 1½ inches to 2¾ inches, and said lens has an arcuate cross-sectional configuration, wherein the arc length (L1) of said lens is in the range of from about 5½ inches to 7 inches, the improvement comprising at least one concave ventilation indentation in the bottom edge of each of said right and left lens regions.

* * * * *

UNITED STATES PATENT AND TRADEMARK OFFICE
CERTIFICATE OF CORRECTION

PATENT NO.   : 5,208,614
DATED        : May 4, 1993
INVENTOR(S)  : James H. Jannard It is certified that error appears in the above-identified patent and that said Letters Patent is hereby corrected as shown below:

Column 7, line 61, "about 1 * inches, and" should read "about 1-3/4 inches, and".

Column 8, line 29, "lowermost bottom edge" should read "lowest bottom edge".

Column 8, line 32, "of 1/4 to about" should read "of about 1/4 inch to about".

Column 8, line 36, "if in the range" should read "is in the range".

Column 9, line 16, "left of right lens region" should read "left or right lens region".

Column 9, line 39, "of the wearer" should read "of a wearer".

Column 10, line 42, "of about 178 inches" should read "of about 1/2 inch".

Signed and Sealed this

Nineteenth Day of April, 1994

*Attest:*

BRUCE LEHMAN

*Attesting Officer*   Commissioner of Patents and Trademarks